US010219918B2

(12) United States Patent
LaBelle et al.

(10) Patent No.: US 10,219,918 B2
(45) Date of Patent: Mar. 5, 2019

(54) PROSTHETIC LIMB STRUCTURE AND FABRICATION METHOD

(71) Applicant: Arizona Board of Regents on behalf of Arizona State University, Scottsdale, AZ (US)

(72) Inventors: Jeffrey LaBelle, Tempe, AZ (US); Sarah McBryan, Phoenix, AZ (US)

(73) Assignee: ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 5 days.

(21) Appl. No.: 15/257,462

(22) Filed: Sep. 6, 2016

(65) Prior Publication Data
US 2017/0065439 A1 Mar. 9, 2017

Related U.S. Application Data

(60) Provisional application No. 62/213,983, filed on Sep. 3, 2015.

(51) Int. Cl.
*A61F 2/50* (2006.01)
*A61F 2/60* (2006.01)
(52) U.S. Cl.
CPC .............. *A61F 2/5046* (2013.01); *A61F 2/60* (2013.01); *A61F 2002/607* (2013.01)
(58) Field of Classification Search
CPC .... A61F 2/5046; A61F 2/60; A61F 2002/607; B42D 15/00
See application file for complete search history.

(56) References Cited

U.S. PATENT DOCUMENTS 4,055,690 A * 10/1977 Patterson ................. G09F 1/06
229/92.8

OTHER PUBLICATIONS

Author Unknown, "Flexure Test," Instron, available at least as early as Mar. 24, 2016, 3 pages, http://www.instron.us/en-us/our-company/library/test-types/flexure-test.

(Continued)

*Primary Examiner* — Bruce E Snow
*Assistant Examiner* — Melissa Hoban
(74) *Attorney, Agent, or Firm* — Withrow & Terranova, P.L.L.C.; Vincent K. Gustafson

(57) ABSTRACT

A prosthetic device including an internal frame assembled from multiple longitudinal members and multiple transverse members, wherein each member is substantially planar and defines peripheral slots, and wherein the longitudinal members and transverse members are arranged to mate with one another to join the longitudinal members with the transverse members. In certain embodiments, a first group of longitudinal members is radially arranged relative to a central axis extending through the transverse members, and a second group of longitudinal members is tangentially arranged relative to the central axis, preferably with lateral edges of the second group of longitudinal members extending between two different longitudinal members of the first group of longitudinal members to provide enhanced torsional rigidity. An outer shaping member, which may be tubular in shape, may be arranged to cover at least a portion of the internal frame.

18 Claims, 17 Drawing Sheets

(56) References Cited

OTHER PUBLICATIONS

Biddiss, Elaine A. et al., "Upper limb prosthesis use and abandonment: A survey of the last 25 years," Prosthetics and Orthotics International, vol. 31, No. 3, Sep. 2007, pp. 236-257.
Carey, Stephanie L. et al., "Golf hand prosthesis performance of transradial amputees," Prosthetics and Orthotics International, vol. 39, No. 3, Feb. 2014, 4 pages.
Chiu, James et al., "Prediction of upper extremity impact forces during falls on the outstretched hand," Journal of Biomechanics, vol. 31, No. 12, Dec. 1998, pp. 1169-1176.
Cignoni, Paolo et al., "Field Aligned Mesh Joinery," ACM Transactions on Graphics, vol. 28, No. 4, Article 106, Aug. 2009, 13 pages.
Cignoni, Paolo et al., "Mesh Joinery: A Method for Building Fabricable Structures," European Research and Innovation, ERCIM News, vol. 101, 2015, pp. 44-45.
Davidson, Judith, "A Survey of the Satisfaction of Upper Limb Amputees with Their Prostheses, Their Lifestyles, and Their Abilities," Journal of Hand Therapy, vol. 15, No. 1, Mar. 31, 2002, pp. 62-70.
Gretsch, Kendall F. et al., "Development of novel 3D-printed robotic prosthetic for transradial amputees," Prosthetics and Orthotics International, vol. 40, No. 3, Jun. 1, 2016, Published Online May 1, 2015, 4 pages.
Herbert, Nicholas et al., "A preliminary investigation into the development of 3-D printing of prosthetic sockets," Journal of Rehabilitation Research and Development, vol. 42, No. 2, Mar./Apr. 2005, pp. 141-146.
McGimpsey, Grant et al., "Limb Prosthetics Services and Devices," Bioengineering Institute Center for Neuroprosthetics Worcester Polytechnic Institution, White Paper, 2008, 35 pages.
O'Connell, Colleen, "Upper Limb Prosthetic Services Post Haiti Earthquake: Experiences and Recommendations of Haiti-Based Rehabilitation Program," JPO Journal of Prosthetics and Orthotics, vol. 24, No. 2, Apr. 2012, pp. 77-79.
O'Keeffe, Bernard, "Prosthetic rehabilitation of the upper limb amputee," Indian Journal of Plastic Surgery, vol. 44, No. 2, May/Aug. 2011, pp. 246-252.
O'Neill, Ciaran, "An Advanced, Low Cost Prosthetic Arm," Proceedings of the IEEE Sensors, Nov. 2014, IEEE, pp. 494-498.
O'Sullivan, L.W. et al., "Forearm torque strengths and discomfort profiles in pronation and supination," Ergonomics, vol. 48, No. 6, May 15, 2005, pp. 703-721.
Oh, I. et al., "Proximal strain distribution in the loaded femur. An in vitro comparison of the distributions in the intact femur and after insertion of different hip-replacement femoral components," ABSTRACT, Journal of Bone & Joint Surgery, American Volume, Jan. 1978, 2 pages.
Russell, D. et al., "A Bench-Top Prototype of a Variable Stiffness Prosthesis," MEC '05 Intergrating Prosthetics and Medicine, 2005, UNB, 4 pages.
Schultz, Aimee E. et al., "Expert opinions on success factors for upper-limb prostheses," Journal of Rehabilitation Research and Development, vol. 44, No. 4, 2007, pp. 483-490.
Wijk, Ulrika et al., "Forearm amputees' views of prosthesis use and sensory feedback," Journal of Hand Therapy, vol. 28, No. 3, Jul.-Sep. 2015, pp. 269-278.
Ziegler-Graham, Kathryn et al., "Estimating the prevalence of limb loss in the United States: 2005 to 2050," Archives of Physical Medicine and Rehabilitation, vol. 89, No. 3, Mar. 31, 2008, pp. 422-429.
LaBelle, Jeffrey, "Fishbone Prosthetic," ABSTRACT, Arizona State University, Apr. 23, 2015, 2 pages.

* cited by examiner

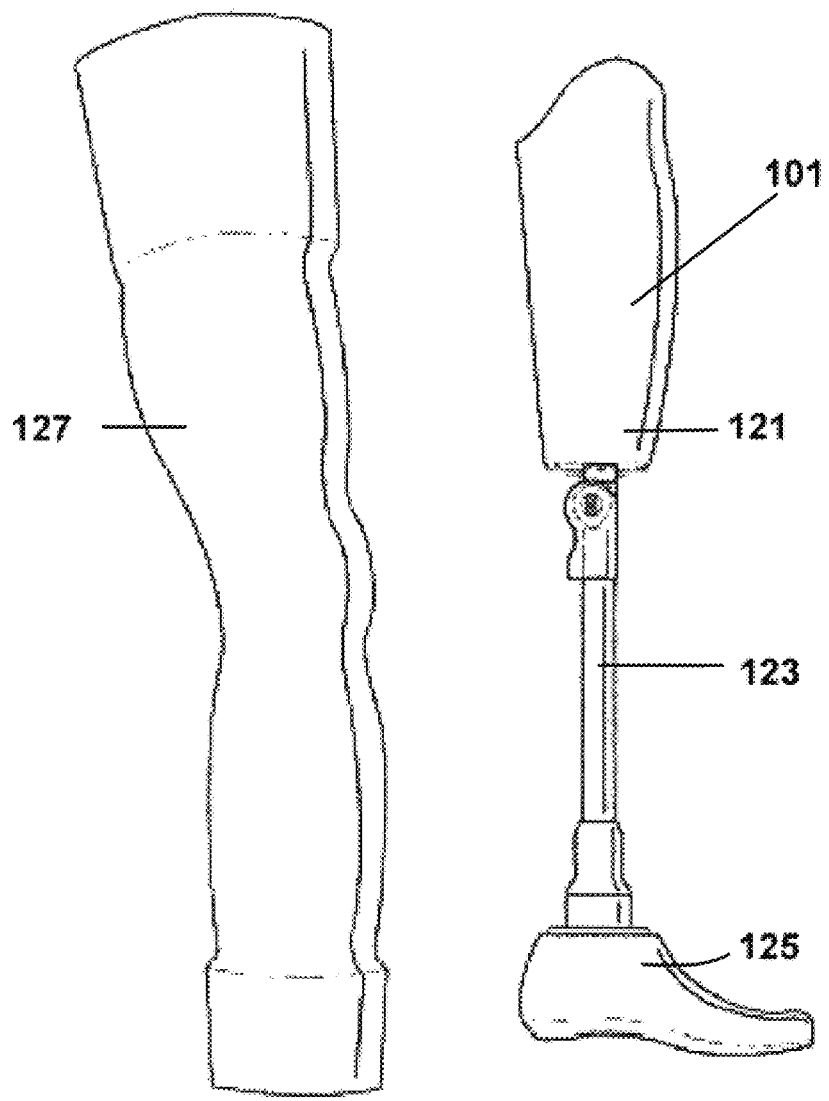
FIG._1
(RELATED ART)

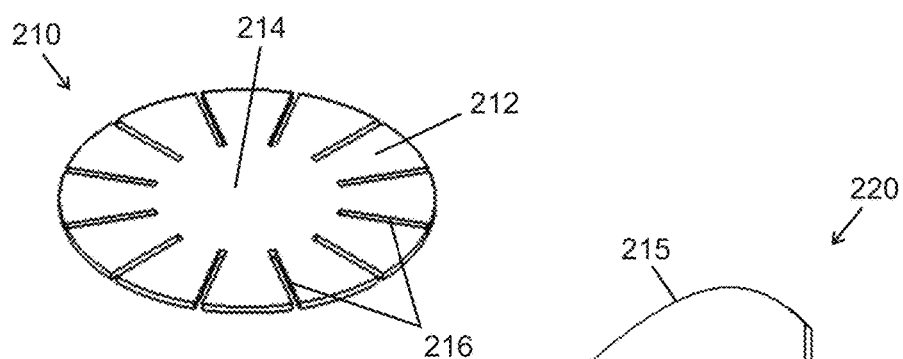
*FIG._2A*
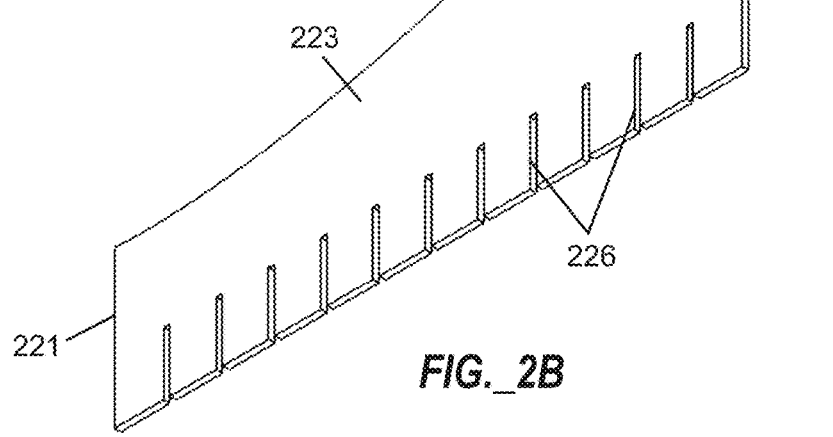
*FIG._2B*
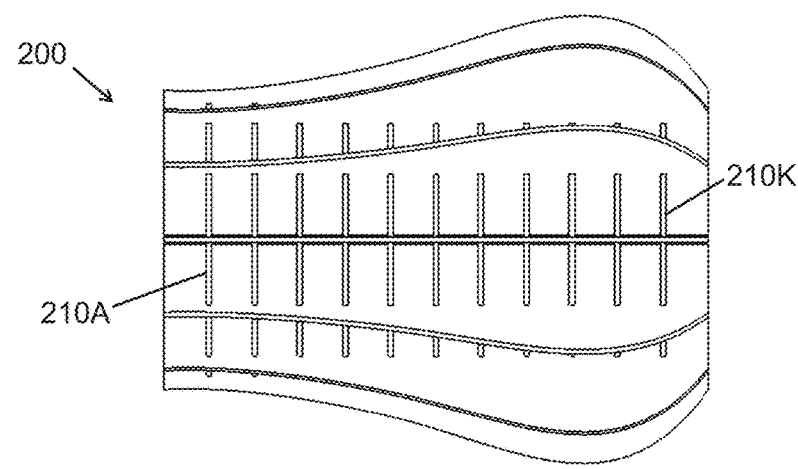
*FIG._2C*

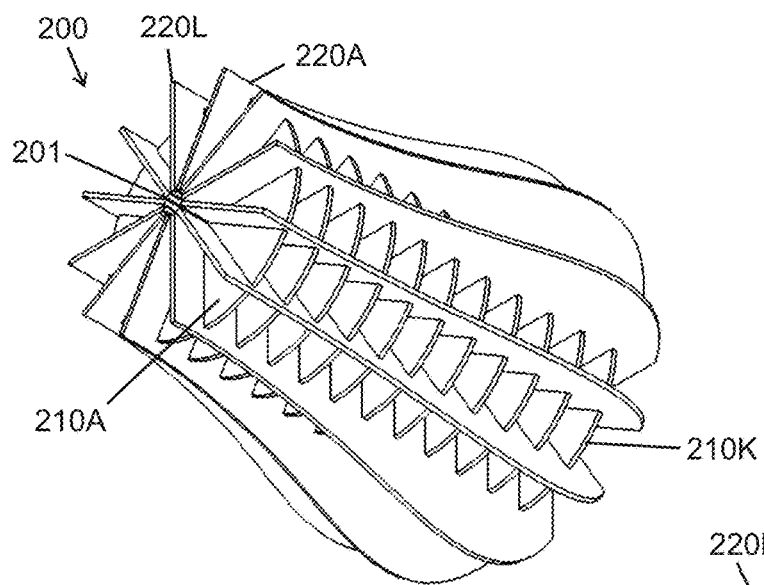
FIG._2E
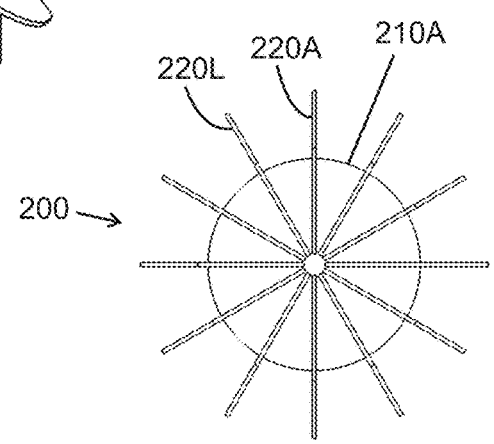
FIG._2D
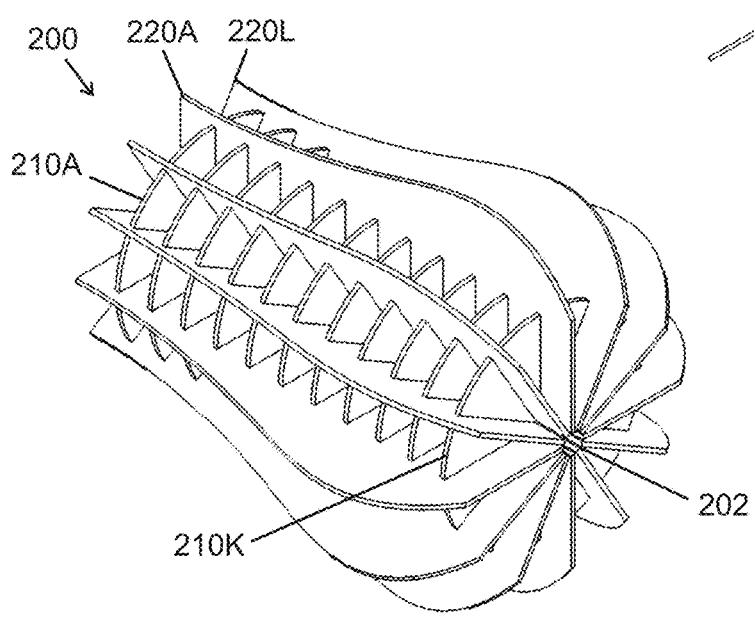
FIG._2F

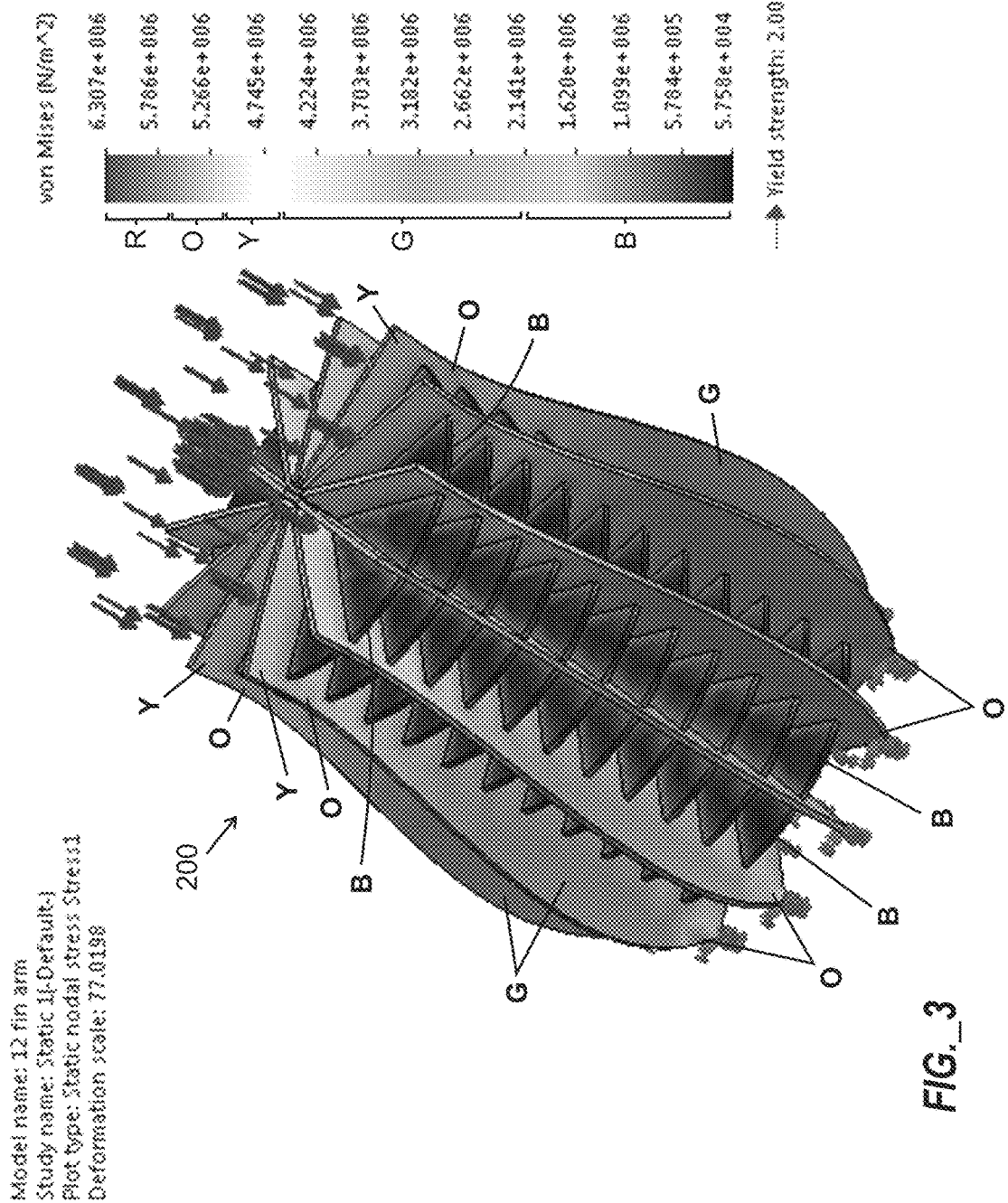
FIG._3

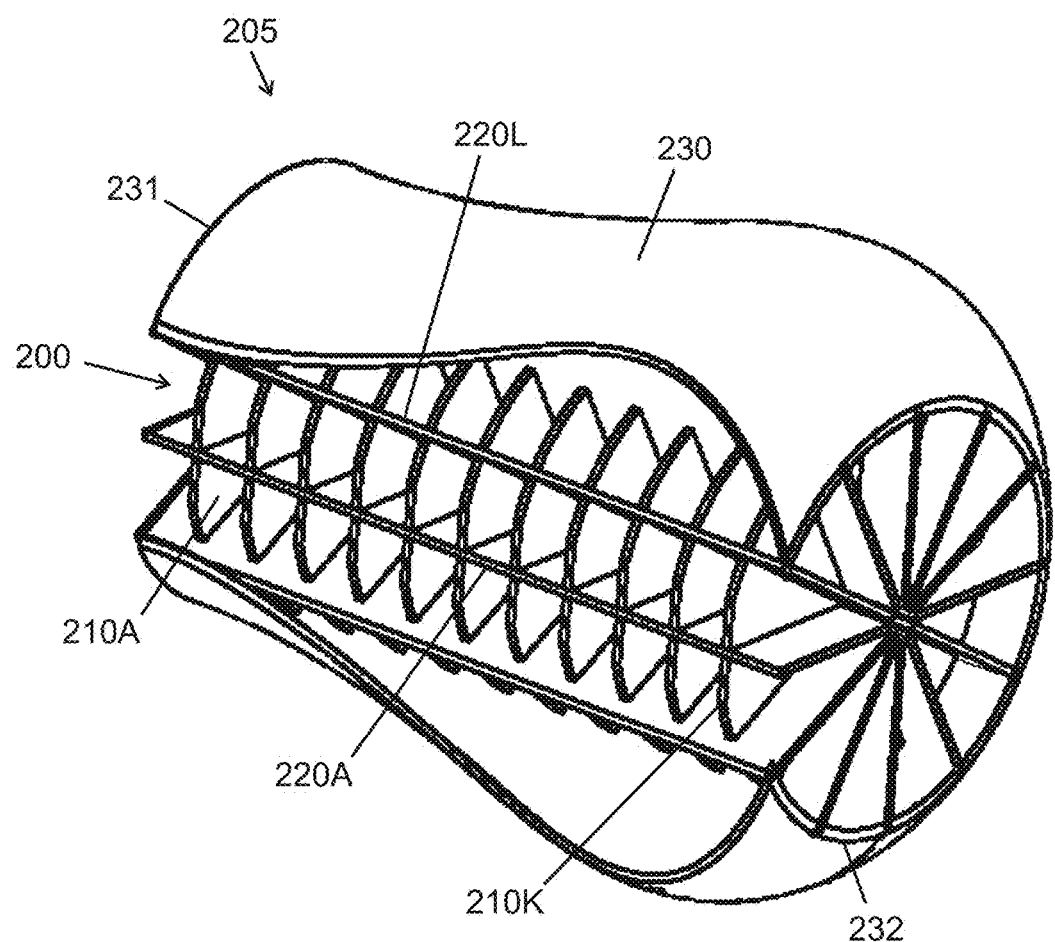
FIG._4A

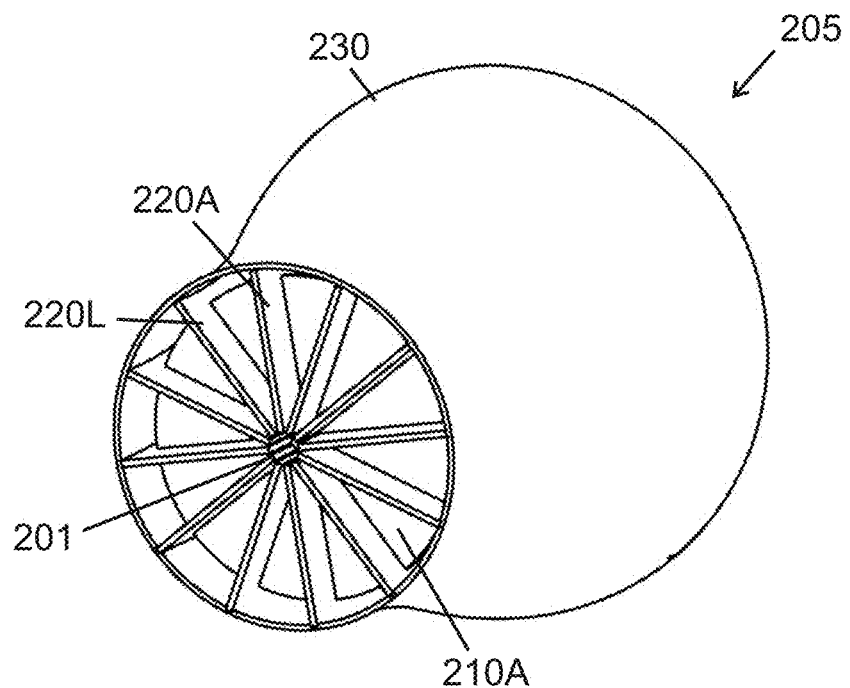
FIG._4B
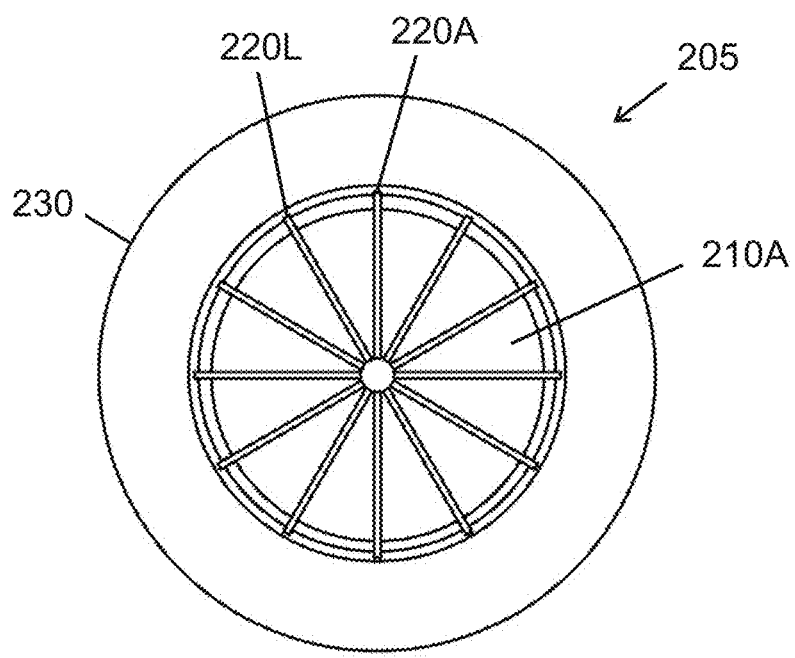
FIG._4C

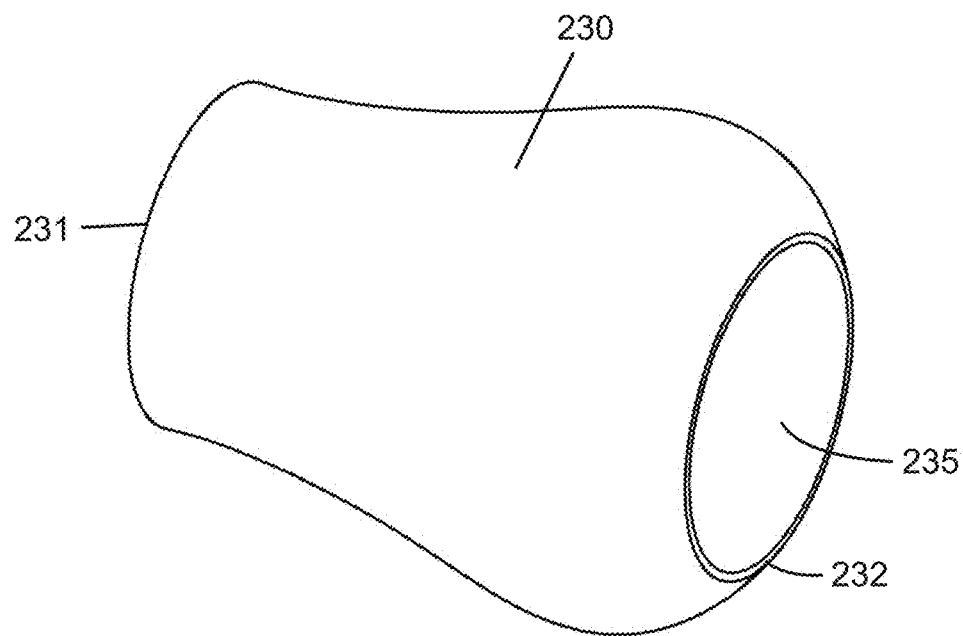
FIG._4D
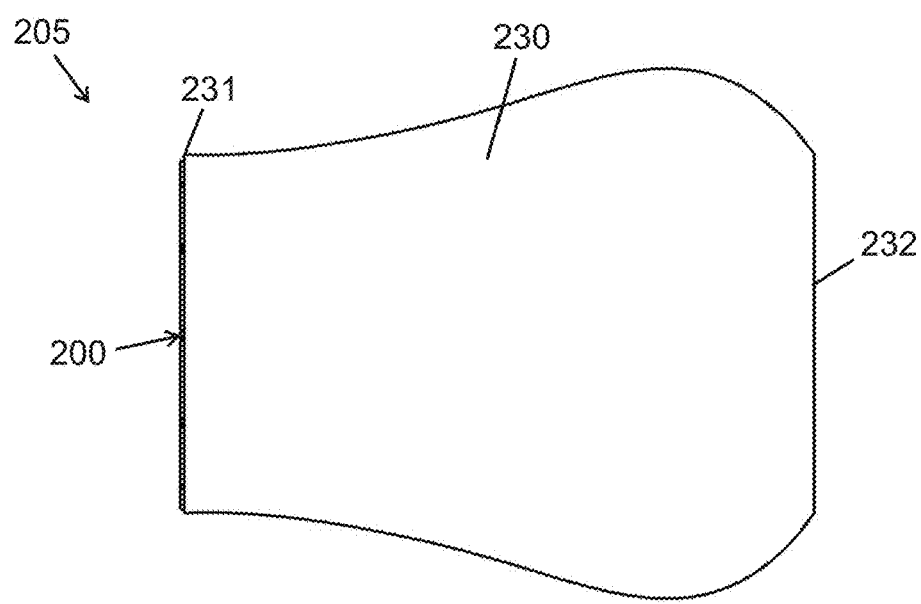
FIG._4E

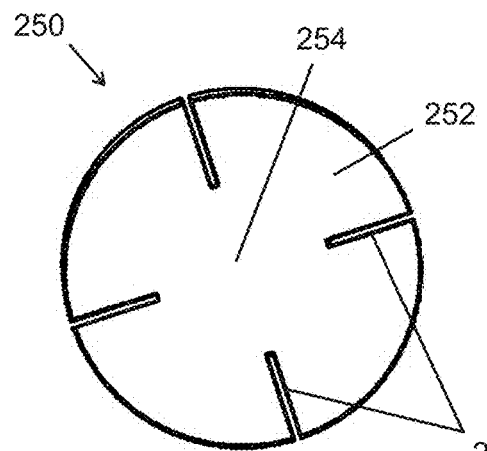
*FIG._5A*
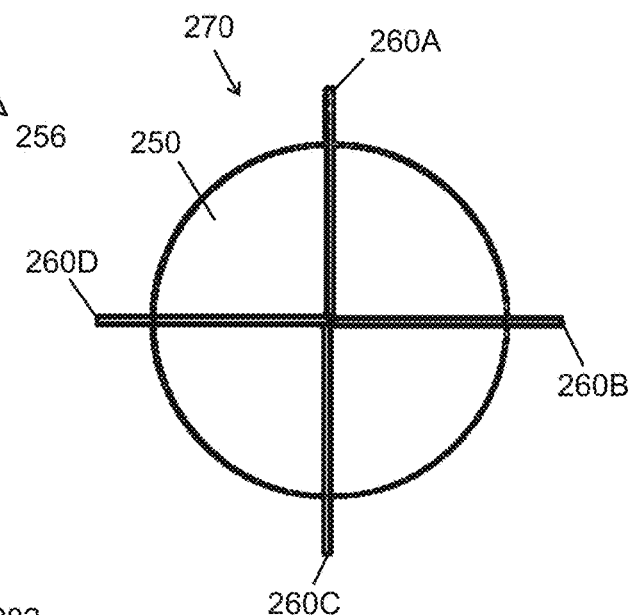
*FIG._5B*
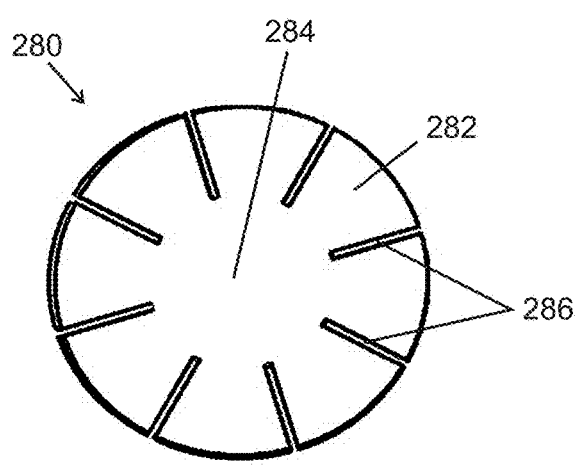
*FIG._6*

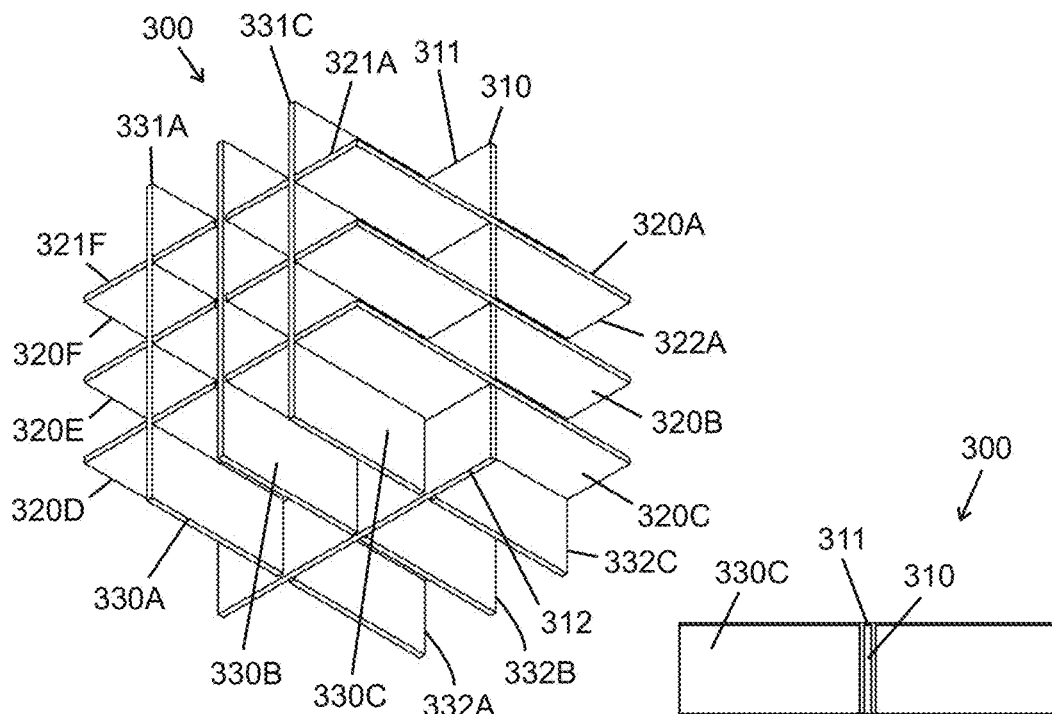
FIG._7A
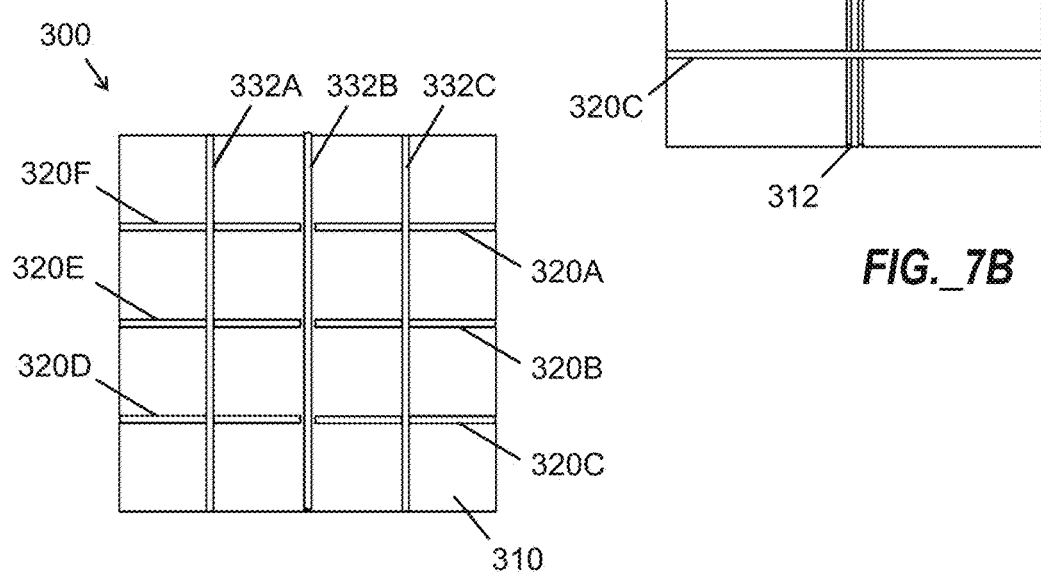
FIG._7B
FIG._7C

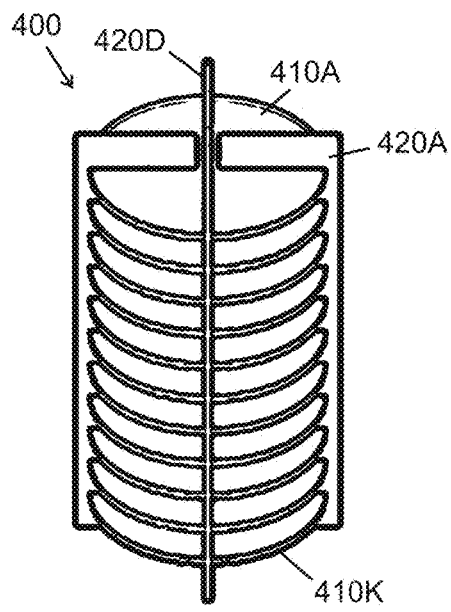
FIG._8
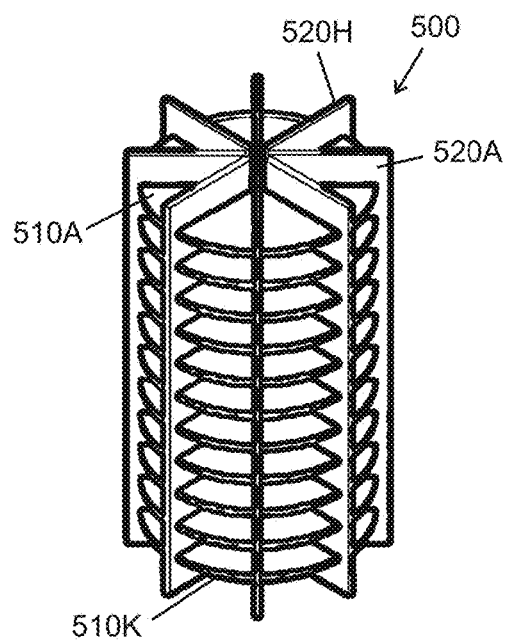
FIG._9
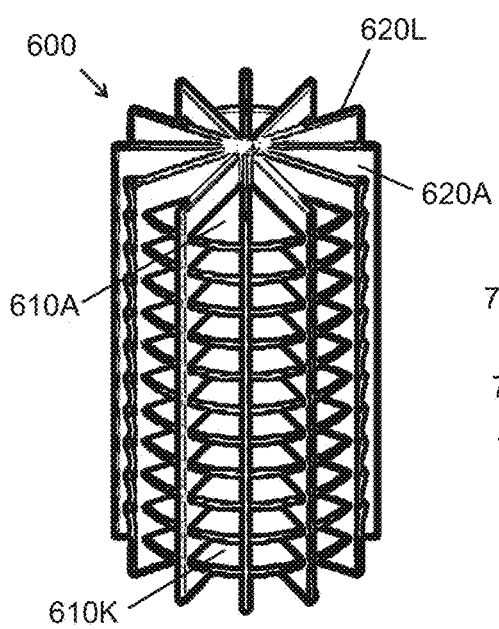
FIG._10
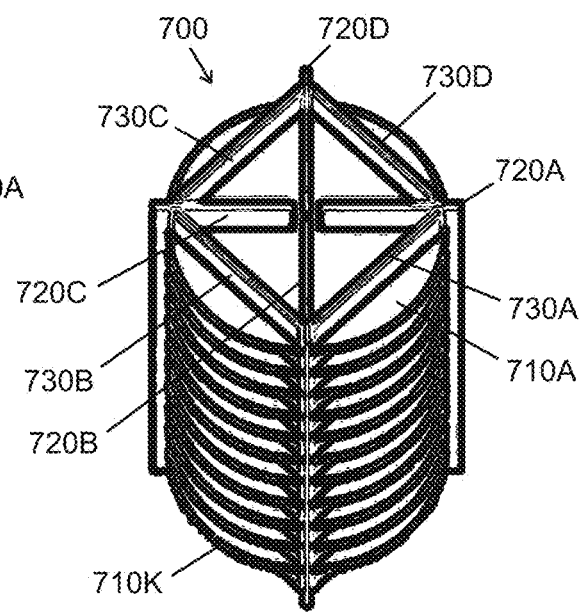
FIG._11

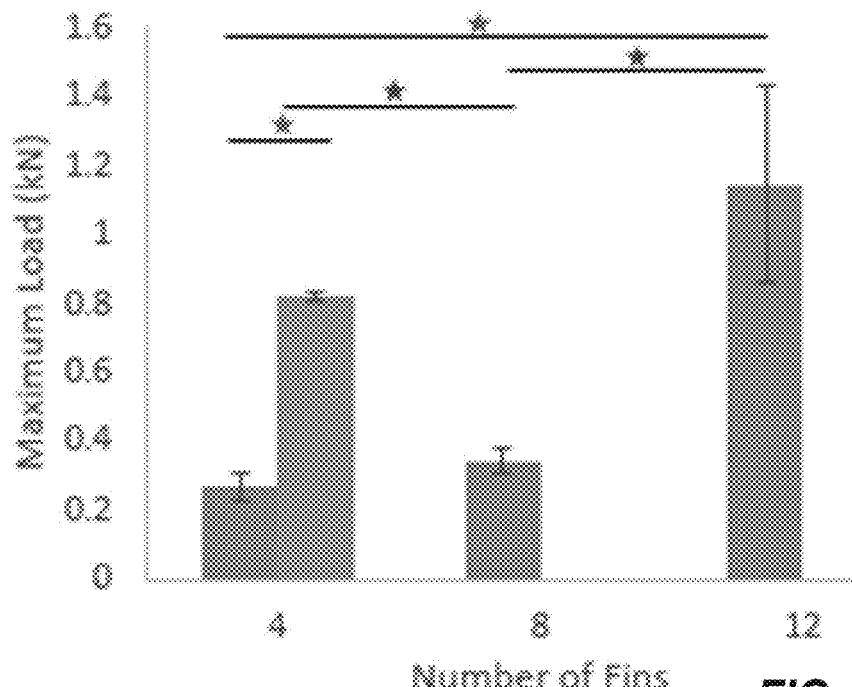
FIG._12
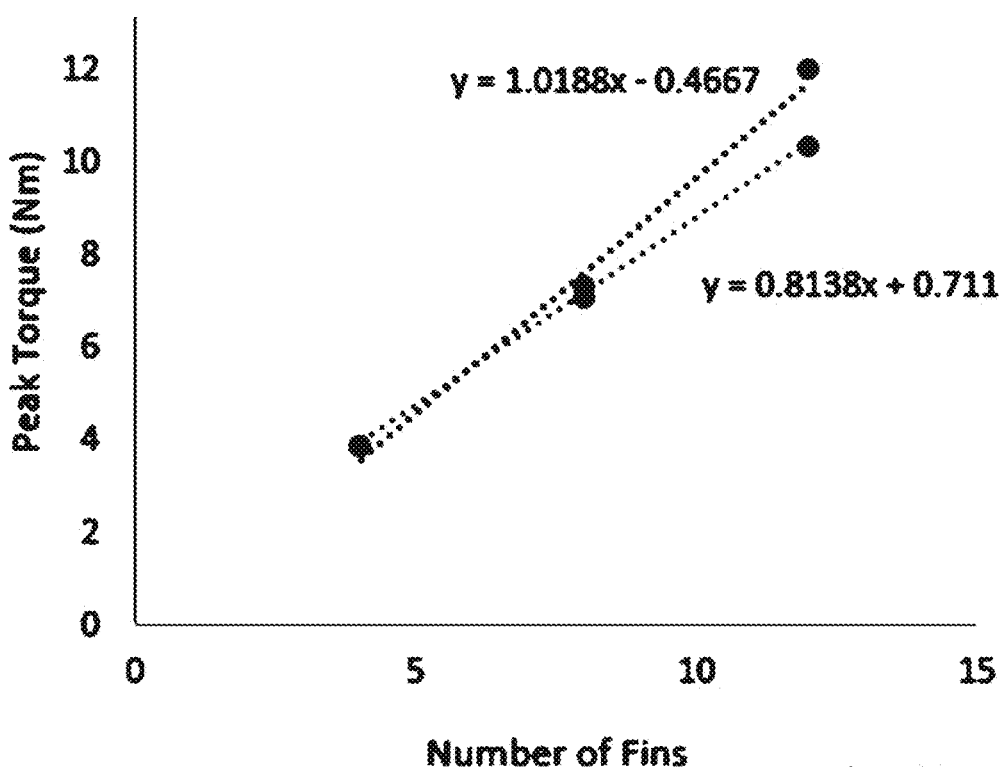
FIG._14

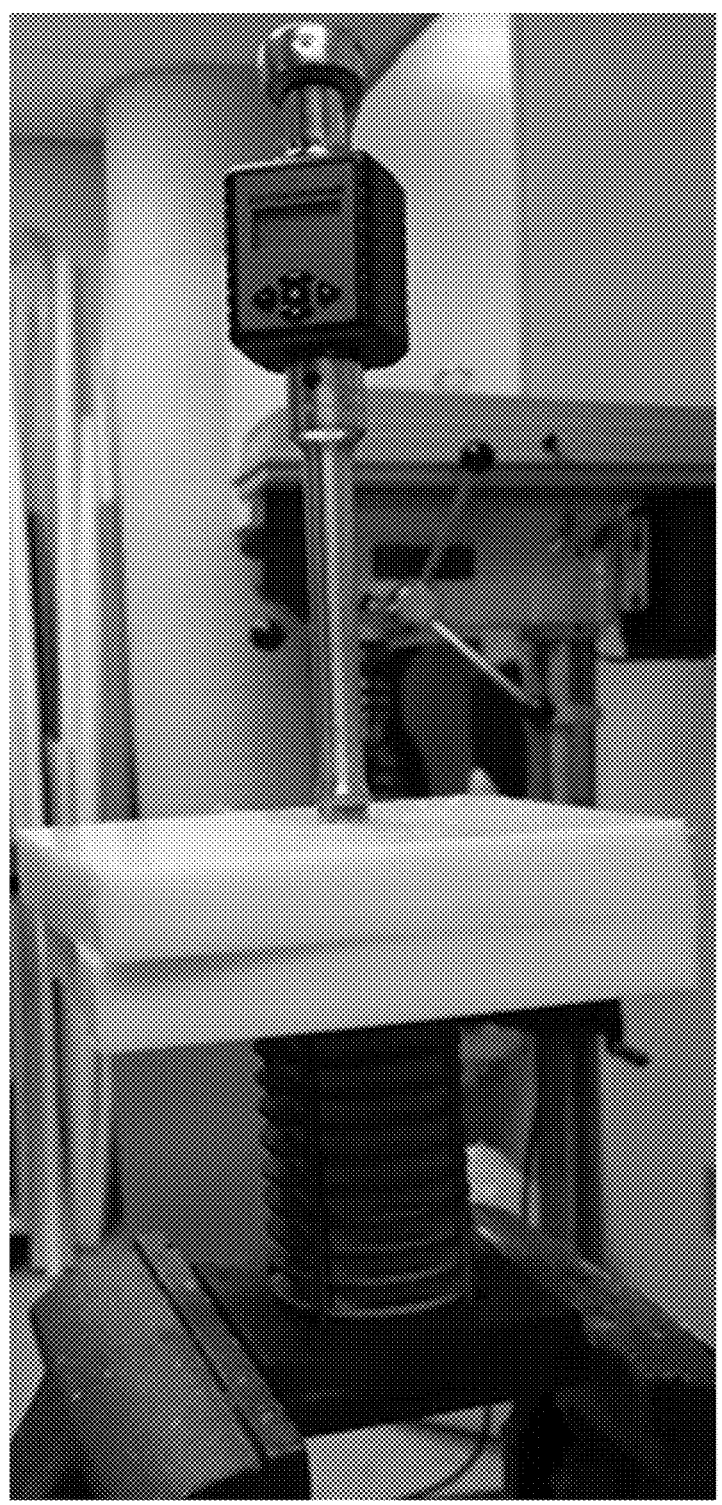
FIG._13

| Sample | % Free space |
|---|---|
| 4 Fin Circle | 90% |
| 8 Fin Circle | 88% |
| 12 Fin Circle | 85% |
| 4T Circle | 86% |
FIG._15
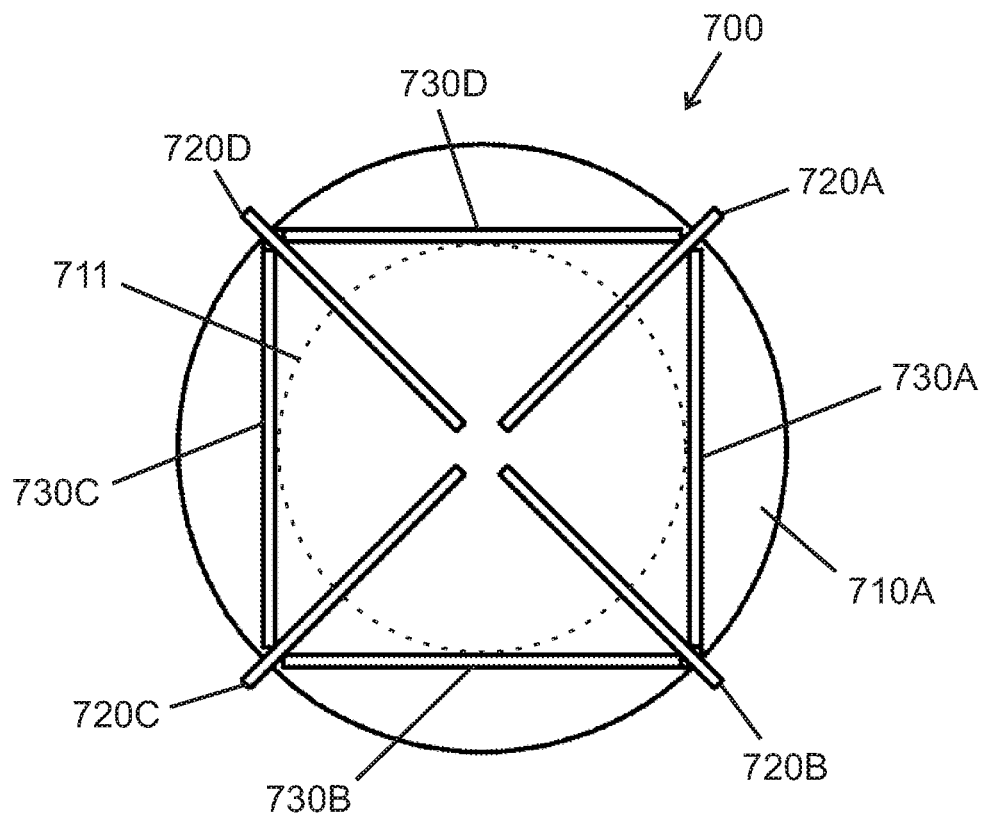
FIG._16A

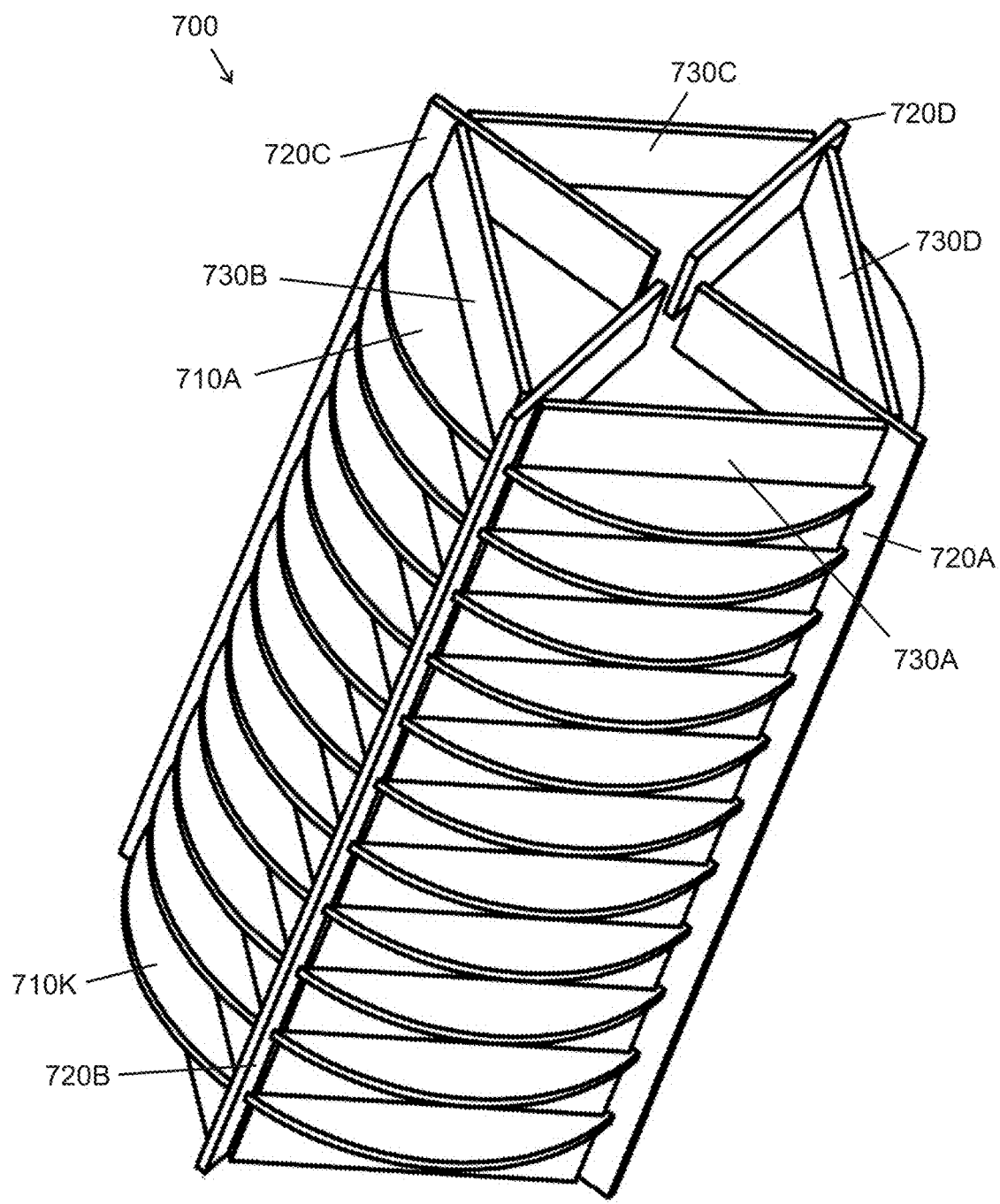
FIG._16B

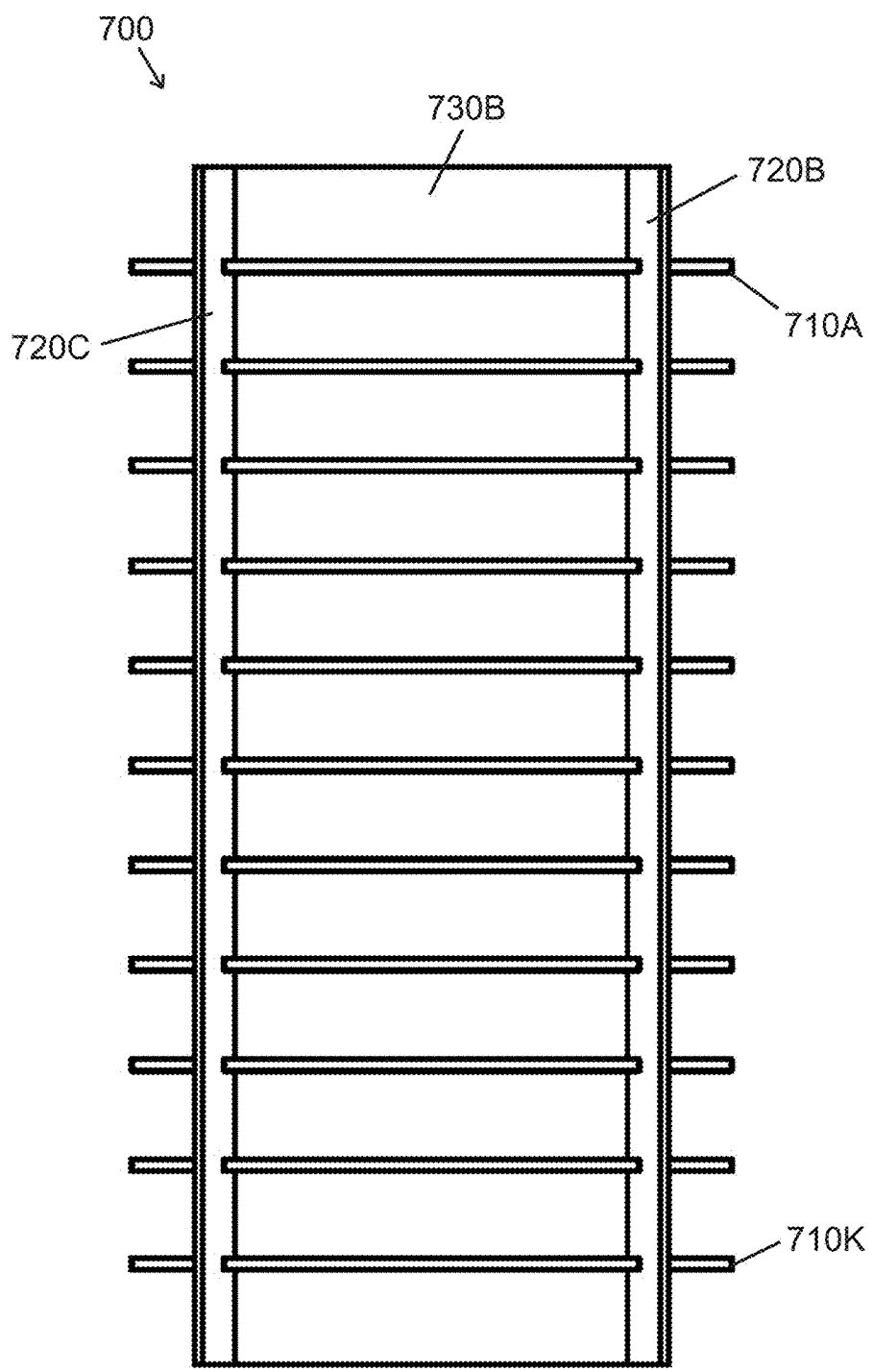
FIG._16C

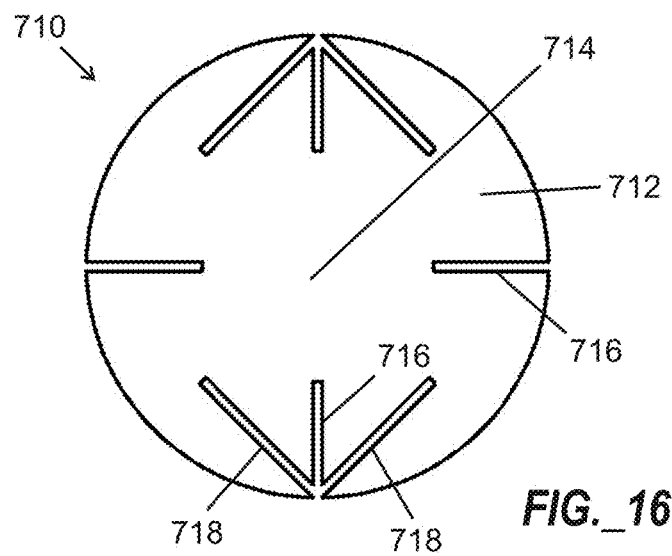
FIG._16D
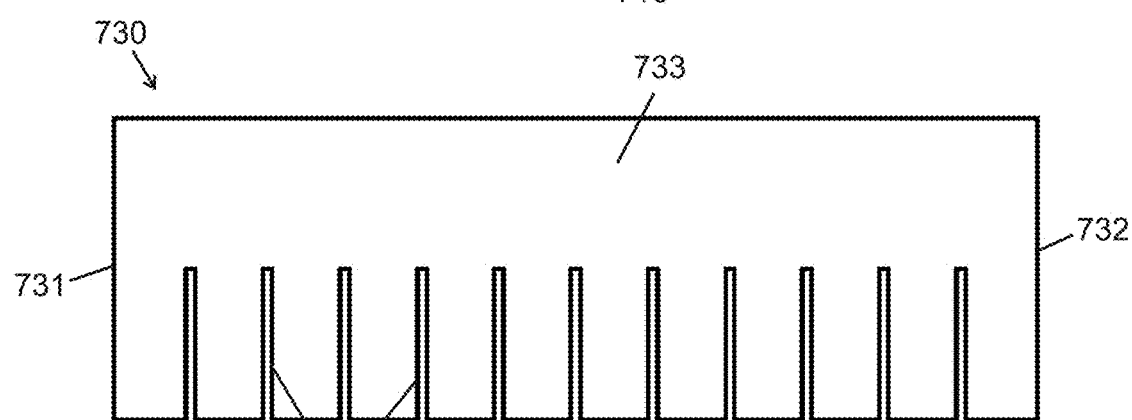
FIG._16E
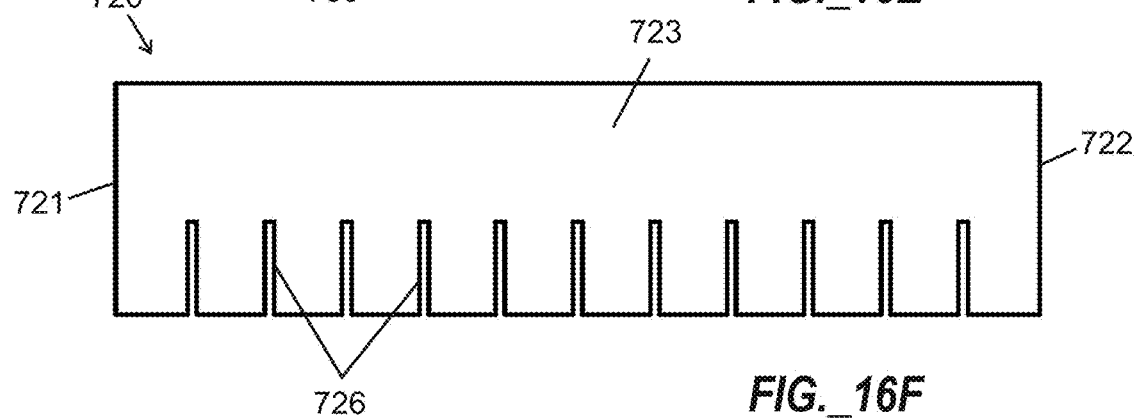
FIG._16F

PROSTHETIC LIMB STRUCTURE AND FABRICATION METHOD

STATEMENT OF RELATED APPLICATIONS

This application claims the benefit of provisional patent application Ser. No. 62/213,983, filed Sep. 3, 2015, the disclosure of which is hereby incorporated herein by reference in its entirety.

TECHNICAL FIELD

This disclosure relates to prosthetic devices, including artificial limbs and portions thereof, and methods for fabricating such devices.

BACKGROUND

Congenital limb defects or losing a limb through an accident can severely impede individuals in carrying out day-to-day tasks. Artificial limbs, or prosthetics, are intended to restore a degree of normal function to amputees or individuals with congenital limb defects. Due to significant variations in sizes and shapes of individuals and their limbs, as well as variations in size and shape of residual limb portions for sufferers of amputation and congenital limb defects, prosthetics are typically custom manufactured for patients.

FIG. 1 shows a conventional prosthetic leg 101 having a socket 121 with a recessed surface arranged to engage an end of a user's amputated limb (e.g., remaining leg portion). The socket 121 may embody a padded plastic structure that distributes compressive forces on the end of the amputated limb. The bottom of the socket 121 is attached to a pylon 123 which may embody a tubular metal support. The bottom of the pylon 123 may attach to an artificial foot 125 that can be a molded plastic structure. The prosthetic leg 101 may include a foam covering 127 that can be attached to the socket 121 and the pylon 123 to provide a more lifelike shape. Components of the prosthetic leg 101 can be coupled together using fasteners such as screws, bolts, and adhesives.

Functional prosthetics include categories of body-powered and externally-powered prosthetics. Body-powered prosthetics typically use cables and harnesses strapped to the individual to mechanically maneuver the artificial limb, but can be fatiguing to operate. Externally powered artificial limbs, including myoelectric prosthetics, seek to reduce user fatigue using batteries and electronic systems to control movement. A myoelectric prosthetic may be attached to a user's remaining limb portion using suction technology, and sensors may be used to detect minute muscle, nerve, and electromyographic activity. Muscle activity triggered by a user is translated into information used by electric motors to control movement of the artificial limb. Myoelectric limbs may look and even move much like a natural limb. The primary disadvantages to such limbs are weight and cost.

Prosthetics with endoskeletal structures or exoskeletal structures are known. Endoskeletal prosthetics include at least one internal support, such as an aluminum, titanium, or carbon fiber pylon. Exoskeletal prosthetics include an outer structure providing structural rigidity, typically including laminated reinforcement materials such as fiberglass, nylon, Dacron®, carbon fiber, and Kevlar®, which may be bound with polymer resin.

Due to their custom character and potentially high complexity, prosthetic devices typically require significant manufacturing time and entail high production costs. Need exists for prosthetic devices and prosthetic device fabrication methods to address limitations of conventional devices and methods.

SUMMARY

Aspects of the disclosure relate to a prosthetic device including an internal frame assembled from multiple longitudinal members and multiple transverse members, wherein each member is substantially planar and defines peripheral slots, and wherein the longitudinal members and transverse members are arranged to mate with one another to join the longitudinal members with the transverse members. In certain embodiments, a first group of longitudinal members is radially arranged relative to a central axis extending through the transverse members, and a second group of longitudinal members is tangentially arranged relative to the central axis, preferably with lateral edges of the second group of longitudinal members extending between two different longitudinal members of the first group of longitudinal members to provide enhanced torsional rigidity. Methods for fabricating a prosthetic device including multiple longitudinal members and multiple transverse members mated together to form an internal frame are also provided. In certain embodiments, an outer shaping member may be arranged to cover at least a portion of the internal frame. At least a portion of the outer shaping member may optionally include a tubular shape.

In one aspect, the disclosure relates to a prosthetic device including an internal frame, wherein the internal frame includes a plurality of longitudinal members and a plurality of transverse members. Each longitudinal member of the plurality of longitudinal members is substantially planar and includes a plurality of first peripheral slots defined through an entire thickness of the respective longitudinal member. Each transverse member of the plurality of transverse members is substantially planar and includes a plurality of second peripheral slots defined through an entire thickness of the respective transverse member. Each first peripheral slot of the plurality of first peripheral slots is arranged to mate with a different second peripheral slot of the plurality of second peripheral slots, to join the plurality of longitudinal members with the plurality of transverse members.

In certain embodiments, at least some transverse members of the plurality of transverse members are arranged along planes substantially parallel to one another. In certain embodiments, at least some transverse members of the plurality of transverse members are arranged substantially perpendicular to the plurality of longitudinal members. In certain embodiments, at least some transverse members of the plurality of transverse members are bonded to the plurality of longitudinal members (e.g., by adhesive bonding, solvent bonding, or thermal bonding).

In certain embodiments, at least some members of (i) the plurality of longitudinal members and/or (ii) the plurality of transverse members comprise one or more of: polymeric materials, paperboard materials, wood fiber-based materials, laminated composite materials, metals, or metallic materials.

In certain embodiments, longitudinal members of the plurality of longitudinal members are arranged with a substantially equal angular distribution relative to or around the plurality of transverse members.

In certain embodiments, at least some longitudinal members (e.g., a first group) of the plurality of longitudinal members are radially arranged relative to a central axis extending through the plurality of transverse members. In certain embodiments, at least some other longitudinal members (e.g., a second group) of the plurality of longitudinal members are tangentially arranged relative to the central axis extending through the plurality of transverse members. In certain embodiments, lateral edges of the second group of longitudinal members extend between two different longitudinal members of the first group of longitudinal members (e.g., to provide enhanced torsional rigidity). In certain embodiments, each transverse member includes a plurality of radially oriented slots arranged to receive a group of radially oriented longitudinal members and includes a plurality of tangentially oriented slots arranged to receive a group of tangentially oriented longitudinal members.

In certain embodiments, a prosthetic device further comprises an outer shaping member arranged to cover at least a portion of the internal frame. In certain embodiments, at least a portion of the outer shaping member comprises a tubular shape.

In another aspect, the disclosure relates to a method for fabricating a prosthetic device utilizing a plurality of substantially planar longitudinal members and a plurality of substantially planar transverse members. Each longitudinal member of the plurality of substantially planar longitudinal members includes a plurality of first peripheral slots defined through an entire thickness of the respective longitudinal member, and each transverse member of the plurality of substantially planar transverse members includes a plurality of second peripheral slots defined through an entire thickness of the respective transverse member. The method includes mating each first peripheral slot of the plurality of first peripheral slots with a different second peripheral slot of the plurality of second peripheral slots to join the plurality of substantially planar longitudinal members with the plurality of substantially planar transverse members to form an internal frame of the prosthetic device.

In certain embodiments, at least some longitudinal members of the plurality of substantially planar longitudinal members are radially arranged relative to a central axis extending through the plurality of substantially planar transverse members, and at least some other longitudinal members of the plurality of substantially planar longitudinal members are tangentially arranged relative to the central axis extending through the plurality of substantially planar transverse members.

In certain embodiments, the method further comprises bonding at least some transverse members of the plurality of substantially planar transverse members to the plurality of substantially planar longitudinal members. In certain embodiments, the bonding comprises at least one of adhesive bonding, solvent bonding, or thermal bonding.

In certain embodiments, the method further comprises providing an outer shaping member to cover at least a portion of the internal frame. In certain embodiments, the outer shaping member is applied over the internal frame by steps including rolling or sliding. In certain embodiments, at least a portion of the outer shaping member comprises a tubular shape.

In certain embodiments, the method further comprises providing at least one of the following elements within one or more spaces between transverse members of the plurality of substantially planar transverse members of the internal frame: an actuator, an energy storage element, a sensor, or a control element.

In certain embodiments, the method further comprises fabricating at least one of the plurality of substantially planar longitudinal elements or the plurality of substantially planar transverse members. In certain embodiments, at least some members of (i) the plurality of substantially planar longitudinal members and/or (ii) the plurality of substantially planar transverse members are fabricated by at least one step selected from thermoforming, molding, stamping, casting, milling, blade cutting, laser cutting, liquid jet cutting, three-dimensional printing, or multi-layer additive material deposition.

In certain embodiments, the method further comprises measuring one or more dimensions of a prosthetic recipient, and fabricating (i) the plurality of substantially planar longitudinal members and/or (ii) the plurality of substantially planar transverse members responsive to said measuring.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

BRIEF DESCRIPTION OF DRAWINGS

FIG. 1 is an elevation view of components of a conventional prosthetic leg.

FIG. 2A is a perspective view of a substantially planar transverse member of a frame of a prosthetic device according to one embodiment, with the transverse member including a generally round body and twelve peripheral slots.

FIG. 2B is a perspective view of a substantially planar longitudinal member of a frame of a prosthetic device according to one embodiment, with the longitudinal member having an asymmetric shape with multiple peripheral slots arranged along one straight edge.

FIG. 2C is a side elevation view of a portion of an internal frame of a prosthetic device including multiple (i.e., eleven) transverse members according to FIG. 2A and multiple (i.e., twelve) longitudinal members according to FIG. 2B mated with one another via the respective peripheral slots.

FIG. 2D is a top plan view of the portion of the internal frame of FIG. 2C.

FIG. 2E is a first perspective view of the portion of the internal frame of FIGS. 2C and 2D.

FIG. 2F is a second perspective view of the portion of the internal frame of FIGS. 2C-2E.

FIG. 3 is a stress diagram obtained by modeling the internal frame of FIGS. 2C-2F with application of a static load of 2000 Newtons.

FIG. 4A is a partially cut-away first perspective view of a portion of a prosthetic device including at least a portion of an internal frame according to FIGS. 2C-2F and further including an outer shaping member arranged over exterior edges of the multiple transverse members.

FIG. 4B is a second perspective view of the portion of the prosthetic device including the outer shaping member of FIG. 4A.

FIG. 4C is a top plan view of the portion of the prosthetic device of FIGS. 4A and 4B.

FIG. 4D is a perspective view of the outer shaping member depicted in FIGS. 4A-4C.

FIG. 4E is a side elevation view of the portion of the prosthetic device of FIGS. 4A-4C.

FIG. 5A is a top plan view of a substantially planar transverse member of an internal frame of a prosthetic device according to one embodiment, with the transverse member being round and including four peripheral slots.

FIG. 5B is a top plan view of the substantially planar transverse member according to FIG. 5A arranged to receive four longitudinal members.

FIG. 6 is a top plan view of a substantially planar transverse member of a frame of a prosthetic device according to one embodiment, with the transverse member being round and including eight peripheral slots.

FIG. 7A is a perspective view of a portion of an internal frame of a prosthetic device including multiple (i.e., six) first rectangular longitudinal members extending in a first direction, multiple (i.e., three) second rectangular longitudinal members extending in a second direction, and one rectangular transverse member bisecting the first and second rectangular longitudinal members.

FIG. 7B is a side elevation view of the portion of the internal frame of FIG. 7A.

FIG. 7C is a top plan view of the portion of the internal frame of FIGS. 7A and 7B.

FIG. 8 is a perspective view of a portion of an internal frame of a prosthetic device according to one embodiment, including eleven round transverse members defining slots arranged to receive corresponding slots of four rectangular longitudinal members that extend radially outward.

FIG. 9 is a perspective view of a portion of an internal frame of a prosthetic device according to one embodiment, including eleven round transverse members defining slots arranged to receive corresponding slots of eight rectangular longitudinal members that extend radially outward.

FIG. 10 is a perspective view of a portion of an internal frame of a prosthetic device according to one embodiment, including eleven round transverse members defining slots arranged to receive corresponding slots of twelve rectangular longitudinal members that extend radially outward.

FIG. 11 is a perspective view of a portion of an internal frame of a prosthetic device according to one embodiment, including eleven round transverse members defining a first group of slots arranged to receive corresponding slots of a first group of four rectangular longitudinal members that extend radially outward, and defining a second group of slots arranged to receive corresponding slots of a second group of four rectangular longitudinal members that extend in a tangential direction.

FIG. 12 is a bar chart showing maximum axial load (in kiloNewtons) versus number of fins for the internal frame portions of FIGS. 8-11.

FIG. 13 is a photograph of a test apparatus applying torque to an internal frame of a prosthetic device including multiple round transverse members defining slots arranged to receive corresponding slots of four rectangular longitudinal members that extend radially outward.

FIG. 14 is a line chart showing peak torque (in Newton-meters) versus number of fins for internal frame portions of different numbers of longitudinal members (or fins).

FIG. 15 is a table identifying percentage free space for the prosthetic device internal frame portions of FIGS. 8-11.

FIG. 16A is a top plan view of the portion of the internal frame according to FIG. 11.

FIG. 16B is a perspective view of the portion of the internal frame of FIG. 16A.

FIG. 16C is a side elevation view of the portion of the internal frame of FIGS. 16A and 16B.

FIG. 16D is a top plan view of a substantially planar transverse member of the portion of the internal frame of FIGS. 16A-16C.

FIG. 16E is a top plan view of a substantially planar longitudinal member arranged to extend in radial direction of the portion of the internal frame of FIGS. 16A-16C.

FIG. 16F is a top plan view of a substantially planar longitudinal member arranged to extend in a tangential direction of the portion of the internal frame of FIGS. 16A-16C.

DETAILED DESCRIPTION

Figure 17:
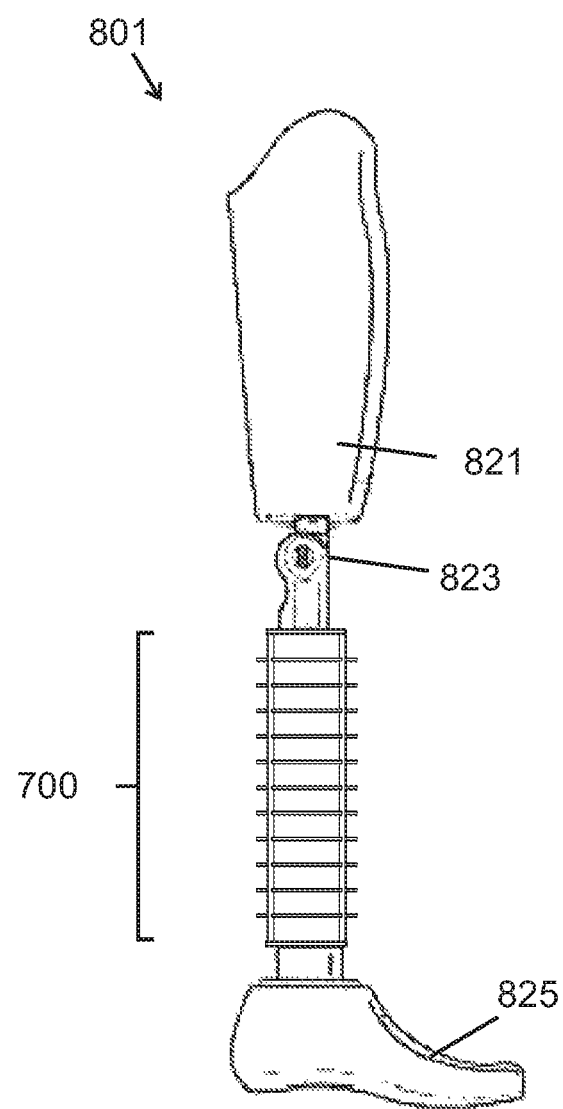
FIG. 17 is an elevation view of a prosthetic device (e.g., a leg) including an internal frame according to FIGS. 16A-16E.

In certain aspects, a prosthetic device includes an internal frame assembled from multiple longitudinal members and multiple transverse members, wherein each member is substantially planar and defines peripheral slots, and wherein the longitudinal members and transverse members are arranged to mate with one another to join the longitudinal members with the transverse members. Prosthetic devices of various shapes and conformations may be fabricated rapidly by producing longitudinal members and transverse members, and then assembling them together to form an internal frame of a prosthetic device. Longitudinal and transverse members of various materials may be used to produce lightweight and crush-resistant structures capable of withstanding substantial axial and torsional loads. Additionally, gaps or spaces between assembled members may be used for receiving functional elements such as actuators (e.g., motors, solenoids, pistons, etc.), energy storage elements (e.g., batteries), control elements, sensors, and the like.

Substantially planar longitudinal members and transverse members can be fabricated using various materials and various fabrication techniques. Examples of materials that may be used according to certain embodiments include, but are not limited to, the following: polymeric materials, fiber-reinforced materials, composites, laminated composites, multi-layer laminates, carbon fiber, paperboard, wood-based materials, fiberglass, metals, metallic materials, and combinations of two or more of the foregoing. Examples of techniques that may be used to produce longitudinal members and transverse members include, but are not limited to, the following: thermoforming, molding, stamping, forging, casting, milling, blade cutting, laser cutting, liquid jet cutting, three-dimensional printing, multi-layer additive material deposition, and combinations of two or more of the foregoing.

The term "substantially planar" as used herein refers to an element preferably having length and width dimensions that substantially exceed a thickness dimension, wherein at least one face is preferably substantially flat in character. In certain embodiments, length and/or width dimensions of substantially planar members disclosed herein each exceed corresponding thickness dimensions by a factor of at least five, at least ten, at least fifteen, at least twenty, at least thirty, at least forty, at least fifty, at least seventy-five, or at least one hundred.

In certain embodiments, at least some transverse members (or all transverse members) may be arranged along planes substantially parallel to one another.

In certain embodiments, at least some transverse members (or all transverse members) may be arranged substantially perpendicular to longitudinal members with which the transverse members are assembled.

In certain embodiments, longitudinal members may be arranged with a substantially equal angular distribution around one or more transverse members. In certain embodiments, longitudinal members may be arranged to extend in a radial direction relative to the transverse members.

In certain embodiments, at least some transverse members of a plurality of transverse members may be bonded to a plurality of longitudinal members. Examples of bonding techniques that may be used include, but are not limited to, adhesive bonding, solvent bonding, thermal bonding, welding, and the combinations of the foregoing. In certain embodiments, two-part adhesives such as epoxies may be used. If employed, adhesives may be applied using techniques such as brushing, spraying, dipping, rolling, or other techniques.

In certain embodiments, one or more outer shaping members may be arranged to cover at least a portion of an internal frame as described herein. In certain embodiments, at least a portion of an outer shaping member may include a tubular shape. In certain embodiments, an outer shaping member may be bonded to outermost surfaces of a frame (e.g., edges of longitudinal and/or transverse members, and/or faces of transverse members). In certain embodiments, an outer shaping member may be removably applied over portions of a frame via methods such as rolling or sliding. In certain embodiments, an outer shaping member may be removably applied over portions of a frame without permanent bonding, such as to permit servicing or replacement of components (e.g., actuators, energy storage elements, sensors, control elements, etc.) that may be arranged in interstices or voids within the internal frame. In certain embodiments, an outer shaping member may be arranged to compress portions of the internal frame to enhance its rigidity and/or inhibit unintended separation between structural members. In certain embodiments, an outer shaping member may embody a substantially continuous material. In other embodiments, an outer shaping member may embody one or more holes or voids.

In certain embodiments, one or more dimensions of a prosthetic recipient may be measured, and longitudinal and/or transverse members may be fabricated responsive to such measurement, with such members being assembled thereafter to form an internal frame of the prosthetic device. In this manner, an internal frame of a prosthetic device may be custom-built for a specific recipient. If a prosthetic recipient has an intact limb, then the intact limb may be measured to permit an internal frame of a prosthetic device to match dimensions of the intact limb as closely as possible.

In certain embodiments, longitudinal members and/or transverse members may include symmetrical length and/or width dimensions. In other embodiments, one or more portions of longitudinal members and/or transverse members may be asymmetric in character.

In certain embodiments, multiple longitudinal members within a single frame may comprise substantially the same dimensions. In other embodiments, different longitudinal members within a single frame may comprise different dimensions relative to one another.

In certain embodiments, multiple transverse members within a single frame may comprise substantially the same dimensions. In other embodiments, different transverse members within a single frame may comprise different dimensions relative to one another.

In certain embodiments, longitudinal members within a single frame may comprise a substantially uniform thickness. In certain embodiments, different longitudinal members within a single frame may comprise different thicknesses. In certain embodiments, thickness of one or more longitudinal members may be subject to vary within each respective longitudinal member.

In certain embodiments, transverse members within a single frame may comprise a substantially uniform thickness. In certain embodiments, different transverse members within a single frame may comprise different thicknesses. In certain embodiments, thickness of one or more transverse members may be subject to vary within each respective transverse member.

In one embodiment, a prosthetic device includes an internal frame, wherein the internal frame includes a plurality of longitudinal members and a plurality of transverse members. Each longitudinal member is substantially planar and includes a plurality of first peripheral slots defined through an entire thickness of the respective longitudinal member. Each transverse member is substantially planar and includes a plurality of second peripheral slots defined through an entire thickness of the respective transverse member. Each first peripheral slot of the plurality of first peripheral slots is arranged to mate with a different second peripheral slot of the plurality of second peripheral slots, to join the plurality of longitudinal members with the plurality of transverse members.

In certain embodiments, each transverse member includes a plurality of radially oriented slots arranged to receive a group of radially oriented longitudinal members and includes a plurality of tangentially oriented slots arranged to receive a group of tangentially oriented longitudinal members.

In one embodiment, a method for fabricating a prosthetic device utilizes a plurality of substantially planar longitudinal members and a plurality of substantially planar transverse members. Each longitudinal member includes a plurality of first peripheral slots defined through an entire thickness of the longitudinal member, and each transverse member includes a plurality of second peripheral slots defined through an entire thickness of the transverse member. The method includes mating each first peripheral slot of the plurality of first peripheral slots with a different second peripheral slot of the plurality of second peripheral slots to join the plurality of longitudinal members with the plurality of transverse members to form an internal frame of the prosthetic device.

FIG. 2A is a perspective view of a substantially planar transverse member 210 of a frame of a prosthetic device according to one embodiment, with the transverse member 210 including a generally round body 212 including a continuous central portion 214 surrounded with a peripheral portion of the body 212 defining twelve peripheral slots 216. As illustrated, the slots 216 are substantially evenly distributed in a radial direction around the perimeter of the transverse member 210. Each slot 216 preferably extends through the entire thickness of the transverse member 210.

FIG. 2B is a perspective view of a substantially planar longitudinal member 220 of a frame of a prosthetic device according to one embodiment. The longitudinal member 220 includes a body 223 has an asymmetric shape with a width that varies between a first end 221 and a second end 222. Multiple peripheral slots 226 are arranged along one straight edge to form a comb-like portion. As illustrated, the slots 226 are substantially evenly distributed along the straight edge. A width of the longitudinal member 220 is greater proximate to the second end 222 than proximate to the first end 221.

FIGS. 2C-2F illustrate a portion of an internal frame 200 of a prosthetic device including multiple (i.e., eleven) transverse members 210A-210K according to FIG. 2A and multiple (i.e., twelve) longitudinal members 220A-220L according to FIG. 2B mated with one another via the respective peripheral slots (i.e., slots 216 illustrated in FIG. 2A and slots 226 illustrated in FIG. 2B. FIG. 2C provides a side elevation view, FIG. 2D provides a top plan view, and FIGS. 2E and 2F provide perspective views of the internal frame. FIG. 2E illustrates an optional first axial plug 201 arranged along a central axis of the internal frame 200, and FIG. 2F illustrates an optional second axial plug 202 located along the central axis between inner edges of the longitudinal members 220A-220L.

FIG. 3 is a stress diagram (converted to grayscale from a diagram originally rendered in color) obtained by modeling the internal frame 200 of FIGS. 2C-2F with application of a static load of 2000 Newtons. The direction of the load is shown by the group of arrows above the topmost end. The legend at right in FIG. 3 includes letters identifying colors as follows: R denotes red, O denotes orange, Y denotes yellow, G denotes green, and B denotes blue. Corresponding letters and lead lines indicating colors have been added to the internal frame 200 shown in FIG. 3. The yield strength of the modeled material was 2.0e+7 Newtons per square meter ($N/m^2$), and modeling indicated that none of the parts of the frame experienced a stress exceeding 5.5 $N/m^2$.

FIG. 4A is a partially cut-away first perspective view of a portion of a prosthetic device 205 including at least a portion of an internal frame 200 according to FIGS. 2C-2F and further including an outer shaping member 230 arranged over exterior edges of the multiple transverse members 210A-210K and further surrounding multiple longitudinal members 220A-220L that are interconnected with the transverse members 210A-210K. The outer shaping member 230 includes a first end 231 and a second end 232, and comprises a diameter or width that varies between the first and second ends 231, 232. FIGS. 4B-4E provide additional views of the prosthetic device 205 including an outer shaping member 230 overlying the internal frame 200 of FIG. 4A, with FIGS. 4B and 4D providing perspective views, FIG. 4C providing a top plan view, and FIG. 4E providing a side elevation view. FIG. 4B further illustrates the optional first axial plug 201 arranged along the central axis of the internal frame 200. FIG. 4D provides a perspective view of the outer shaping member 230 depicted in FIGS. 4A-4C. As shown in FIG. 4D, the outer shaping member 230 may include openings (e.g., opening 235) at one or both ends 231, 232. In certain embodiments, one or both ends 231, 232 may be closed.

Although the preceding embodiments illustrated twelve longitudinal members and eleven transverse members, the number of such members may vary in different embodiments. In certain embodiments, four, six, eight, ten, twelve, or more longitudinal members may be provided, and one, two, three, four, six, eight, ten, or more transverse members may be provided in a single frame.

FIG. 5A is a top plan view of a substantially planar transverse member 250 of a frame of a prosthetic device according to one embodiment. The transverse member 250 includes a generally round body 252 and includes a continuous central portion 254 surrounded with a peripheral portion of the body 252 defining four peripheral slots 256 each extending through the entire thickness of the body 252 and extending through a lateral edge of the body 252. FIG. 5B is a top plan view of at least a portion of an internal frame 270 of a prosthetic device including a transverse member 250 according to FIG. 5A arranged to receive multiple longitudinal members 260A-260D, with slots (not shown) defined in the longitudinal members 260A-260D being arranged to mate with the peripheral slots 256 of the transverse member 250.

FIG. 6 is a top plan view of a substantially planar transverse member 280 of a frame of a prosthetic device according to one embodiment. The transverse member 280 includes a generally round body 282 and includes a continuous central portion 284 surrounded with a peripheral portion of the body 282 defining eight peripheral slots 286 each extending through the entire thickness of the body 282 and extending through a lateral edge of the body 282.

Although various embodiments disclosed herein include transverse members having a generally round shape arranged to receive radially arranged longitudinal members, prosthetic devices according to certain embodiments may include longitudinal and transverse members arranged in other configurations.

FIG. 7A is a perspective view of a portion of an internal frame 300 of a prosthetic device including six first rectangular longitudinal members 320A-320F extending in a first direction, three second rectangular longitudinal members 330A-330C extending in a second direction that is perpendicular to the first direction, and one rectangular transverse member 310 bisecting the first and second rectangular longitudinal members 320A-320F, 330A-330C. The transverse member 310 defines multiple slots (not shown) between a first end 311 and a second end 312, including three slots extending perpendicular to the first and second ends 311, 312 for receiving the second rectangular longitudinal members 330A-330C, and additional slots extending parallel to the first and second ends 311, 312 for receiving the first rectangular longitudinal members 320A-320F. Additional slots are defined in the first rectangular longitudinal members 320A-320F for receiving slots of the second rectangular longitudinal members 330A-330C. Each second rectangular longitudinal member 330A-330C includes a first end 331A-331C that is generally adjacent to a corresponding first end 321A-321F of each first rectangular longitudinal member 320A-320F, and each second rectangular longitudinal member 330A-330C includes a second end 332A-332C that is generally adjacent to a corresponding second end 322A-322F of each first rectangular longitudinal member 320A-320F. Although only a single transverse member 310 is illustrated, it is to be appreciated that additional transverse members may be provided in certain embodiments. Additionally, the length and/or width of the internal frame 300 may be adjusted as required to suit a particular dimensional need. FIGS. 7B and 7C provide side elevation and top plan views, respectively, of the portion of the internal frame 300 of FIG. 7A.

FIG. 8 is a perspective view of a portion of an internal frame 400 of a prosthetic device according to one embodiment, including eleven round transverse members 410A-410K defining slots arranged to receive corresponding slots of four rectangular longitudinal members 420A-420D that extend radially outward from a central longitudinal axis of the internal frame 400.

FIG. 9 is a perspective view of a portion of an internal frame 500 of a prosthetic device according to one embodiment, including eleven round transverse members 510A-510K defining slots arranged to receive corresponding slots of eight rectangular longitudinal members 520A-520H that extend radially outward from a central longitudinal axis of the internal frame 500.

FIG. 10 is a perspective view of a portion of an internal frame 600 of a prosthetic device according to one embodiment, including eleven round transverse members 610A-610K defining slots arranged to receive corresponding slots of twelve rectangular longitudinal members 620A-620L that extend radially outward from a central longitudinal axis of the internal frame 600.

FIG. 11 is a perspective view of a portion of an internal frame 700 of a prosthetic device according to one embodiment, including eleven round transverse members 710A-710K defining a first group of slots arranged to receive corresponding slots of a first group of four rectangular longitudinal members 720A-720D that extend radially outward from a central longitudinal axis of the internal frame 700, and defining a second group of slots arranged to receive corresponding slots of a second group of four rectangular longitudinal members 730A-730D that extend in a tangential direction relative to a central longitudinal axis of the internal frame 700. As shown, each rectangular longitudinal member of the second group of four rectangular longitudinal members 730A-730D is arranged 45 degrees apart from two adjacent rectangular longitudinal members of the first group of four rectangular longitudinal members 720A-720D, wherein lateral edges of the second group of four rectangular longitudinal members 730A-730D extend between and contact two different longitudinal members of the first group of four longitudinal members 720A-720D to provide enhanced torsional rigidity. When viewed from above, the first group of four rectangular longitudinal members 720A-720D forms an "X" shape, and the second group of four rectangular longitudinal members 730A-730D forms a square shape, with portions of the "X" shape extending radially outward through corners of the square shape. Additional details of the internal frame 700 are shown in FIGS. 16A-16F.

FIG. 12 is a bar chart showing maximum axial load (in kiloNewtons) versus number of fins for the internal frame portions of FIGS. 8-11. The leftmost bar corresponds to the internal frame 400 shown in FIG. 8; the next bar to the right corresponds to the internal frame 700 shown in FIG. 11; the next bar to the right corresponds to the internal frame 500 shown in FIG. 9; and the rightmost bar corresponds to the internal frame 600 shown in FIG. 10. It is apparent that the internal frame 700 of FIG. 11 (including first and second groups of rectangular longitudinal members 720A-720D, 730A-730D) significantly enhances axial loading strength relative to the frame 400 shown in FIG. 8.

FIG. 13 is a photograph of a test apparatus applying torque to an internal frame of a prosthetic device including multiple round transverse members defining slots arranged to receive corresponding slots of four rectangular longitudinal members that extend radially outward. A vertical torque sensor was used to find peak torque values. Endcaps were created to apply to each frame, and the bottom was fixed. Torque was applied to 95% of an area of the longitudinal members.

FIG. 14 is a line chart showing peak torque (in Newton-meters) versus number of fins for internal frame portions of different numbers of longitudinal members (or fins), for values obtained using the test apparatus of FIG. 13. Generally, increasing the number of fins corresponded to improved peak torque values.

FIG. 15 is a table identifying percentage free space for the prosthetic device internal frame portions of FIGS. 8-11, respectively. Generally, increasing the number of "fins" or longitudinal members resulted in reduction of free space within a frame. Free space within the frame of a prosthetic device may be useful for receiving items such as actuators, energy storage elements, sensors, and control elements.

FIGS. 16A-16C provide top plan, perspective, and side elevation views of the portion of the internal frame 700 according to FIG. 11. Eleven round transverse members 710A-710K include a first group of slots arranged to receive corresponding slots of a first group of four rectangular longitudinal members 720A-720D that extend radially outward from a central longitudinal axis of the internal frame 700, and include a second group of slots arranged to receive corresponding slots of a second group of four rectangular longitudinal members 730A-730D that extend in a tangential direction relative to an imaginary circle 711 (shown in FIG. 16A) concentrically arranged with a central longitudinal axis of the internal frame 700. Referring to FIG. 16A, the first group of four rectangular longitudinal members 720A-720D forms an "X" shape, and the second group of four rectangular longitudinal members 730A-730D forms a square shape, with portions of the "X" shape extending radially outward through corners of the square shape. The imaginary circle 711 has a diameter smaller than a lateral extent of at least one (e.g., first) transverse member 710A. As further shown in FIG. 16A, each rectangular longitudinal member 730A-730D extending in a tangential direction is arranged in contact with two different rectangular longitudinal members 720A-720D.

FIG. 16D is a top plan view of a substantially planar transverse member 710 of the portion of the internal frame 700 of FIGS. 16A-16C. The transverse member 710 includes a generally round body 712 including a continuous central portion 714 surrounded with a peripheral portion of the body 712 defining four radially extending peripheral slots 716 (i.e., extending a radial direction relative to a central axis definable through the body 712) and defining four tangential slots 718 that extend in a direction generally tangential to the central axis. As illustrated, each tangential slot 718 is arranged 45 degrees apart from an adjacent peripheral slot 716. Each slot 716, 718 extends through the entire thickness of the transverse member 710.

FIG. 16E is a top plan view of a substantially planar longitudinal member 730 arranged to be received by a tangential slot 718 defined in the transverse member 710 of FIG. 16D, to extend in a tangential direction of the portion of the internal frame 700 of FIGS. 16A-16C. The longitudinal member 730 is generally rectangular in shape, with a body 733 extending between first and second ends 731, 732, and multiple peripheral slots 736 defined along one edge through a thickness of the body 733 and extending in a direction generally parallel with the first and second ends 731, 732.

FIG. 16F is a top plan view of a substantially planar longitudinal member 720 arranged to be received by a radially extending peripheral slot 716 defined in the transverse member 710 of FIG. 16D, to extend in a radial direction of the portion of the internal frame 700 of FIGS. 16A-16C. The longitudinal member 720 is generally rectangular in shape, with a body 723 extending between first and second ends 721, 722, and multiple peripheral slots 726 defined along one edge through a thickness of the body 723 and extending in a direction generally parallel with the first and second ends 721, 722.

FIG. 17 shows a prosthetic device (e.g., prosthetic leg) 801 having a socket 821 with a recessed surface arranged to engage an end of a user's amputated limb (e.g., remaining leg portion). A bottom of the socket 821 may be attached to a joint 823 that is coupled with an internal frame 700 (as described hereinabove in connection with FIGS. 16A-16F). The bottom of the internal frame 700 may attach to an artificial foot 825 that can be a molded plastic structure. The prosthetic leg 801 may include an outer shaping member (not shown) to compress portions of the internal frame 700 and enhance its rigidity and/or inhibit separation between structural members of the internal frame 700.

Technical benefits of frames disclosed herein include: high compressive strength, comparable torsional strength, and high interstitial free space volume; ease of scalability and/or tailoring to individual patients; and rapid and economical production.

Those skilled in the art will recognize improvements and modifications to the preferred embodiments of the present disclosure. All such improvements and modifications are considered within the scope of the concepts disclosed herein and the claims that follow. Any of the various features and elements as disclosed herein may be combined with one or more other disclosed features and elements unless indicated to the contrary herein.

What is claimed is:

1. A prosthetic device sized and shaped to correspond to at least a portion of a limb of a human user, the prosthetic device comprising:
    an internal frame, wherein the internal frame comprises:
        a plurality of longitudinal members, wherein each longitudinal member of the plurality of longitudinal members is substantially planar and comprises a plurality of first peripheral slots defined through an entire thickness of the respective longitudinal member; and
        a plurality of transverse members, wherein each transverse member of the plurality of transverse members is substantially planar and comprises a plurality of second peripheral slots defined through an entire thickness of the respective transverse member; and
    an outer shaping member configured to cover and compress at least portions of the internal frame;
    wherein each first peripheral slot of the plurality of first peripheral slots is arranged to mate with a different second peripheral slot of the plurality of second peripheral slots, to join the plurality of longitudinal members with the plurality of transverse members;
    wherein at least some longitudinal members of the plurality of longitudinal members are radially arranged relative to a central axis extending through the plurality of transverse members; and
    wherein at least some other longitudinal members of the plurality of longitudinal members are tangentially arranged relative to an imaginary circle concentrically arranged with the central axis, wherein the imaginary circle comprises a diameter smaller than a lateral extent of a transverse member of the plurality of transverse members.

2. The prosthetic device of claim 1, wherein at least some transverse members of the plurality of transverse members are arranged substantially perpendicular to the plurality of longitudinal members.

3. The prosthetic device of claim 1, wherein at least some transverse members of the plurality of transverse members are bonded to the plurality of longitudinal members.

4. The prosthetic device of claim 1, wherein at least some members of (i) the plurality of longitudinal members and/or (ii) the plurality of transverse members comprise polymeric materials.

5. The prosthetic device of claim 1, wherein at least some members of (i) the plurality of longitudinal members and/or (ii) the plurality of transverse members comprise paperboard materials, wood fiber-based materials, or laminated composite materials.

6. The prosthetic device of claim 1, wherein at least some members of (i) the plurality of longitudinal members and/or (ii) the plurality of transverse members comprise metals or metallic materials.

7. The prosthetic device of claim 1, wherein at least a portion of the outer shaping member comprises a tubular shape.

8. The prosthetic device of claim 1, wherein each tangentially arranged longitudinal member is arranged in contact with two different radially arranged longitudinal members.

9. The prosthetic device of claim 1, wherein the plurality of longitudinal members comprises at least eight longitudinal members.

10. The prosthetic device of claim 1, further comprising a socket arranged to engage an end of an amputated limb of the human user.

11. The prosthetic device of claim 1, further comprising at least one of the following elements within one or more spaces between transverse members of the plurality of substantially planar transverse members of the internal frame: an actuator, an energy storage element, a sensor, or a control element.

12. A method for fabricating a prosthetic device, utilizing a plurality of substantially planar longitudinal members wherein each longitudinal member of the plurality of substantially planar longitudinal members comprises a plurality of first peripheral slots defined through an entire thickness of the respective longitudinal member, and utilizing a plurality of substantially planar transverse members wherein each transverse member of the plurality of substantially planar transverse members comprises a plurality of second peripheral slots defined through an entire thickness of the respective transverse member, the method comprising:
    mating each first peripheral slot of the plurality of first peripheral slots with a different second peripheral slot of the plurality of second peripheral slots to join the plurality of substantially planar longitudinal members with the plurality of substantially planar transverse members to form an internal frame of the prosthetic device; and
    providing an outer shaping member to cover and compress at least a portion of the internal frame;
    wherein each first peripheral slot of the plurality of first peripheral slots is mated with a different second peripheral slot of the plurality of second peripheral slots;
    wherein at least some longitudinal members of a plurality of longitudinal members are radially arranged relative to a central axis extending through a plurality of transverse members; and
    wherein at least some other longitudinal members of the plurality of longitudinal members are tangentially arranged relative to an imaginary circle concentrically arranged with the central axis, with the imaginary circle comprising a diameter smaller than a lateral extent of a transverse member of the plurality of transverse members.

13. The method of claim 12, wherein at least some transverse members of the plurality of substantially planar transverse members are arranged substantially perpendicular to the plurality of substantially planar longitudinal members.

14. The method of claim 12, further comprising bonding at least some transverse members of the plurality of substantially planar transverse members to the plurality of substantially planar longitudinal members.

15. The method of claim 12, further comprising measuring one or more dimensions of a prosthetic recipient, and fabricating (i) the plurality of substantially planar longitudinal members and/or (ii) the plurality of substantially planar transverse members responsive to said measuring.

16. The method of claim 12, further comprising fabricating at least some members of (i) the plurality of substantially planar longitudinal members and/or (ii) the plurality of substantially planar transverse members by at least one step selected from thermoforming, molding, stamping, or casting.

17. The method of claim 12, further comprising fabricating at least some members of (i) the plurality of substantially planar longitudinal members and/or (ii) the plurality of substantially planar transverse members by at least one step selected from milling, blade cutting, laser cutting, or liquid jet cutting.

18. The method of claim 12, further comprising fabricating at least some members of (i) the plurality of substantially planar longitudinal members and/or (ii) the plurality of substantially planar transverse members by at least one step selected from three-dimensional printing or multi-layer additive material deposition.

* * * * *